US008814362B2

(12) United States Patent
Verdooner

(10) Patent No.: US 8,814,362 B2
(45) Date of Patent: Aug. 26, 2014

(54) METHOD FOR COMBINING A PLURALITY OF EYE IMAGES INTO A PLENOPTIC MULTIFOCAL IMAGE

(71) Applicant: Steven Roger Verdooner, Granite Bay, CA (US)

(72) Inventor: Steven Roger Verdooner, Granite Bay, CA (US)

( * ) Notice: Subject to any disclaimer, the term of this patent is extended or adjusted under 35 U.S.C. 154(b) by 74 days.

(21) Appl. No.: 13/708,979

(22) Filed: Dec. 8, 2012

(65) Prior Publication Data
US 2013/0169934 A1 Jul. 4, 2013

Related U.S. Application Data

(60) Provisional application No. 61/568,851, filed on Dec. 9, 2011.

(51) Int. Cl.
*A61B 3/12* (2006.01)
(52) U.S. Cl.
USPC .......................................................... 351/246

(58) Field of Classification Search
USPC ............................ 351/246, 206, 205; 348/47
See application file for complete search history.

(56) References Cited

U.S. PATENT DOCUMENTS

2010/0097573 A1 * 4/2010 Verdooner et al. ............ 351/206

* cited by examiner

*Primary Examiner* — Hung Dang
(74) *Attorney, Agent, or Firm* — Michael Ries

(57) ABSTRACT

A method for combining a plurality of eye images into a plenoptic multifocal image that includes registering the eye images with a plurality of frames into one or more eye image sets with a processor and a memory system, aligning each of the eye images in each of the one or more image sets with a selected reference that resides on the memory system with the processor and determining one or more in-focus regions of the eye images by calculating one or more gradient images while ignoring noise and other imaging artifacts. The method also includes identifying the one or more in-focus regions with highest resolution from the one or more gradient images and selecting one or more corresponding in-focus intensities from the frames to combine into a plenoptic multifocal image with a higher resolution than the eye images, the frames and the one or more eye image sets.

29 Claims, 4 Drawing Sheets

007# METHOD FOR COMBINING A PLURALITY OF EYE IMAGES INTO A PLENOPTIC MULTIFOCAL IMAGE

This application claims priority to U.S. Provisional Application 61/568,851 filed on Dec. 9, 2011, the entire disclosure of which is incorporated by reference.

TECHNICAL FIELD & BACKGROUND

1. Field of the Invention

The present invention is a method for combining a plurality of eye images. More specifically, the present invention is a method for combining a plurality of eye images into a plenoptic multifocal image.

2. Description of the Related Art

Imaging of an eye is typically done with one or more slit lamps, one or more ophthalmoscopes, one or more fundus cameras, one or more scanning laser ophthalmoscopes or SLO's and one or more wide field eye imaging devices that typically acquire a single image. Even when movies or multiple images are acquired they are often at a specific focal plane. When retinal images are shot with different focus and alignment, it is often up to an observer to view multiple images to combine a composite in their mind of the focus regions. While some of these devices allow control of focus, it is difficult to obtain a well-focused image throughout the thickness of a retina or other ocular region. Additionally, there are optical aberrations that can be caused by the eye imaging device that can cause regions to be out of focus. Alignment of the eye imaging device to a patient's eye also can affect overall clarity of regions of images.

BRIEF SUMMARY OF THE INVENTION

The present invention is a method for combining a plurality of eye images. More specifically, the present invention is a method for combining a plurality of eye images into a plenoptic multifocal image.

The present invention can be utilized in a variety of different operating modalities and in combination with a number of different devices including one or more slit lamp mounted cameras, one or more slit lamp integrated cameras, one or more fundus cameras, one or more ultra-wide field scanning or OPTOS® wide-field devices, hand-held retinal imaging devices, one or more direct ophthalmoscopes, one or more indirect ophthalmoscopes, one or more scanning laser ophthalmoscopes or one or more generic microscopes, one or more endoscopic probes or one or more optical heads (similar to a fundus camera) attached to a separate chinrest-joystick assembly. Each of these modalities and devices allows for registration of one or more image data sets and subsequent image processing to obtain high-frequency in-focus, well-exposed regions from each image data set, combined into a single image or a plenoptic multifocal image, or movie image that allows the user to step through select regions to be viewed that are in focus. The one or more image data sets are registered using image processing algorithms on a computer. One or more control points to determine the amount of registration may be manually set by human observation or automatically calculated by an algorithm.

The present invention utilizes the following image processing steps. First, align each image in the one or more image data sets with respect to a selected reference. The overall method will correct for translation, rotation, perspective changes and intra-frame warping. Second, determine one or more in-focus regions of each frame by calculating a plurality of gradient information while ignoring noise and one or more other imaging artifacts. Third, from the gradient information identify the one or more in-focus regions with a highest magnitude. Fourth, select a plurality of corresponding in-focus intensities from the frames to combine into a multifocal image. The images can be combined in a number of ways, for example by taking the most in-focus point for each area of the image, or by averaging multiple in-focus regions to improve the signal-to-noise ratio.

The present invention differs from traditional eye imaging methods that do not account for visualization of multiple in-focus regions of the retina or other ocular region. The present invention solves this problem through creating an image registration in combination with image analysis and image processing to yield a plurality of high quality focused plenoptic multifocal images and movies. By creating these multiple images, overall resolution and image quality is greatly improved. The present invention can also be utilized with or without discreet focus control.

An object of the present invention is to provide a method for combining a plurality of eye images into a plenoptic multifocal image that can be utilized in combination with one or more eye imaging modalities including but not limited to color fundus imaging, anterior segment imaging, cornea and lens imaging, fluorescein angiography, Indocyanine green or ICG angiography, curcumin fluorescence imaging, autofluorescence, discreet wavelength imaging, red-free imaging, hyper and multi-spectral imaging and optical coherence tomography.

Another object of the present invention is to provide a method for combining a plurality of eye images into a plenoptic multifocal image with improved resolution, improved focus and increased image quality than a traditional photographic ocular image.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
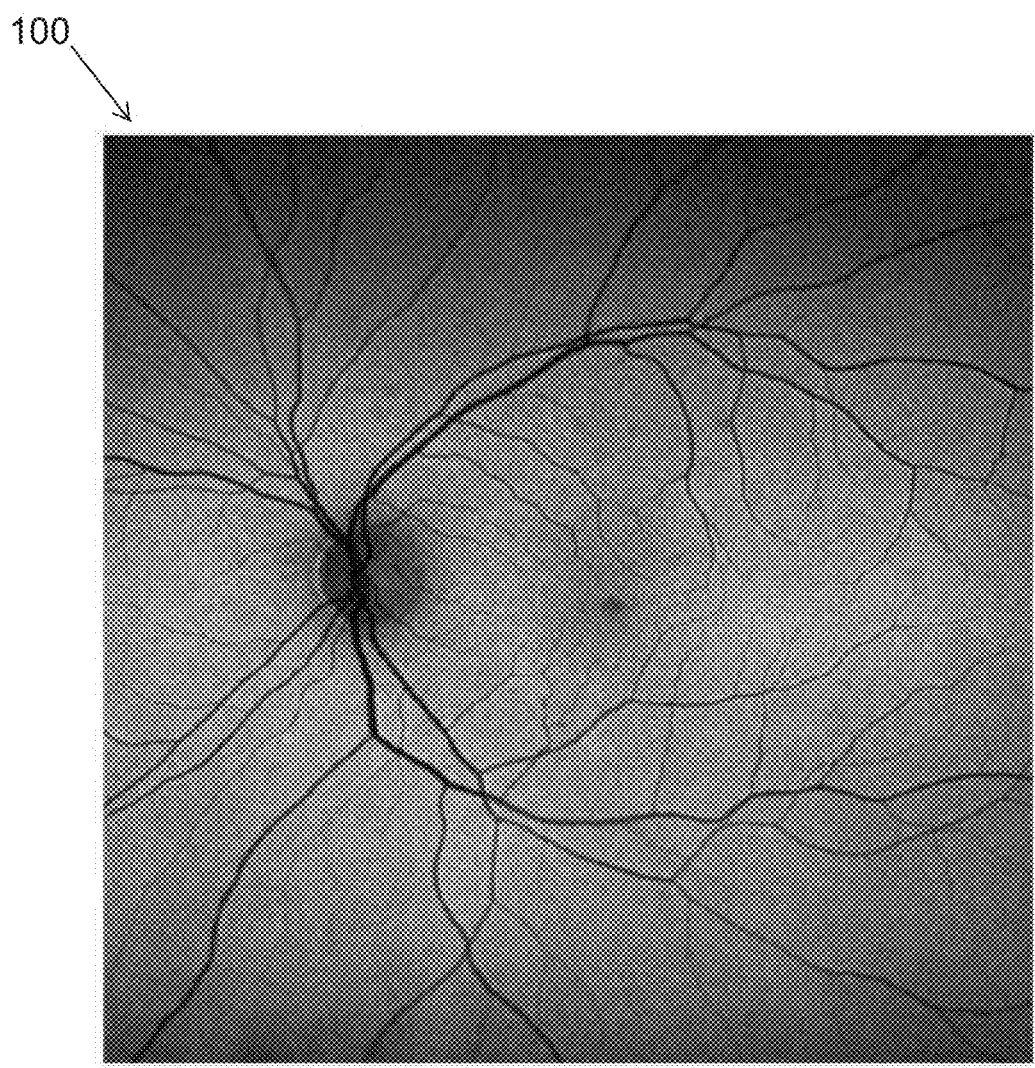
FIG. 1 illustrates a photographic ocular image, in accordance with one embodiment of the present invention.

FIG. 1 illustrates a photographic ocular image 100, in accordance with one embodiment of the present invention.

The photographic ocular image 100 is generated by one or more traditional eye imaging modalities or devices such as one or more slit lamp mounted cameras, one or more slit lamp integrated cameras, optical coherence tomography or OCT, optical imaging at specific wavelengths, multispectral imaging, hyper spectral imaging, autofluorescence imaging, confocal retinal imaging, scanning laser ophthalmoscopy, one or more adaptive optics devices, one or more polarization orientation specific devices, one or more fundus cameras, one or more hand held imagers, one or more direct and indirect ophthalmoscopes, fluorescein angiography, ICG angiography, curcumin fluorescence imaging, autofluorescence and other suitable traditional eye imaging modalities and devices. The photographic ocular image 100 generated in FIG. 1 is a fundus autofluorescence image but can be any photographic ocular image generated by one or more traditional eye imaging modalities or devices such as one or more slit lamp mounted cameras, one or more slit lamp integrated cameras, optical coherence tomography or OCT, optical imaging at specific wavelengths, multispectral imaging, hyper-spectral imaging, autofluorescence imaging, confocal retinal imaging, scanning laser ophthalmoscopy, one or more adaptive optics devices, one or more polarization orientation specific devices, one or more fundus cameras, one or more hand held imagers, one or more direct and indirect ophthalmoscopes, fluorescein angiography, ICG angiography or curcumin fluorescence imaging, or autofluorescence. The images are automatically aligned by computer. This is achieved by taking each frame and comparing it to a reference. First the overall translation, rotation and perspective changes are corrected. The amount of correction is determined by identifying the shift between various common features in the images utilizing feature detection or cross-correlation. Then the images are broken into small sub-regions and the shift between corresponding sub-regions is determined. The shifts for each sub-region are used to warp each part of the image in a continuous manner such that features in the resulting image are aligned with the reference image. The aligned image may also be combined with the reference image to produce a more accurate reference for subsequent use with other frames. The eye images are combined by averaging multiple in-focus regions to improve a signal-to-noise ratio or SNR. The SNR can be defined as 20*log 10 (standard_deviation_image/standard_deviation_noise) with units of dB. The photographic ocular image 100 illustrated in FIG. 1 has an estimated SNR of 10 dB.

Figure 2:
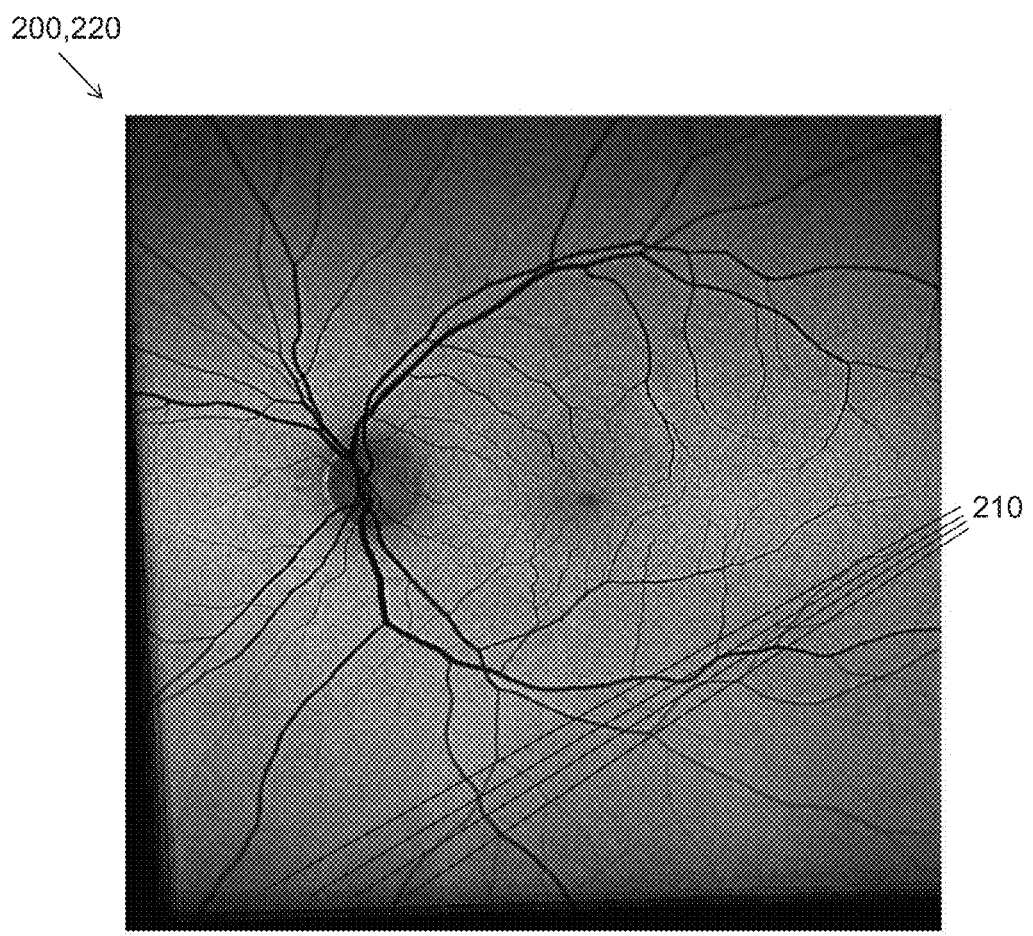
FIG. 2 illustrates a photographic image of a plurality of eye images that are formed into a plenoptic multifocal image, in accordance with one embodiment of the present invention.

FIG. 2 illustrates a photographic image 200 of a plurality of eye images 210 that are formed into a plenoptic multifocal image 220, in accordance with one embodiment of the present invention.

The photographic image 200 of the eye images 210 into the plenoptic multifocal image 220 illustrated and described in FIG. 2 and its description is similar to the photographic ocular image 100 illustrated and described in FIG. 1 and its description. In contrast to the photographic ocular image 100 illustrated and described in FIG. 1 and its description, the photographic image 200 of the eye images 210 into the plenoptic multifocal image 220 illustrated and described in FIG. 2 and its description has been generated by a method for combining a plurality of eye images into a plenoptic multifocal image (FIG. 3 and FIG. 4, 300, 400). The method for combining a plurality of eye images into a plenoptic multifocal image (FIG. 3 and FIG. 4, 300, 400) generates the plenoptic multifocal image 220 that has relatively higher resolution, relatively better focus and relatively better image quality than the photographic ocular image 100 illustrated and described in FIG. 1 and its description. Additional details regarding the method for combining a plurality of eye images into a plenoptic multifocal image (FIG. 3 and FIG. 4, 300, 400) are illustrated and described in subsequent FIG. 3 and FIG. 4 and its description. The photographic ocular image 200 illustrated in FIG. 2 is a 15 frame, aligned, averaged and enhanced image with an estimated SNR of 42 dB.

In another embodiment of the present invention, the method for combining a plurality of eye images into a plenoptic multifocal image can be for imaging eye documentation of an eye's anatomy and/or detection of eye pathology. The method for combining a plurality of eye images into a plenoptic multifocal image can be utilized for imaging an anterior segment, a posterior segment and a substructure of an eye as seen in OCT. One feature of the method for combining a plurality of eye images into a plenoptic multifocal image is an automated registration of images and then subsequent image processing to identify regions that are well-focused, evenly illuminated and to obtain high frequency image information (e.g. using a frequency domain filter or a Weiner filter.) and recombine the processed images into a single image. An algorithm is also capable of eliminating areas of the images that are poorly focused, contain other optical aberrations and/or are not well illuminated. The well-focused regions are identified from the regions with the largest calculated gradient magnitude. The evenly illuminated regions are determined by over-smoothing the image and comparing the average intensity with the overall image intensity. Those regions significantly below the average are considered poorly illuminated and should be excluded from analysis. High frequency image information is calculated by removing one or more low frequency image components and by smoothing and suppressing one or more random noise variations. A multi-scale gradient calculation is one method of obtaining high frequency image information. The high frequency image information is an indication of when the image is in-focus. Poorly focused images or regions will have lower magnitude gradients compared to an in-focus frame. These parts will be excluded from the analysis.

In another embodiment of the present invention, the method for combining a plurality of eye images into a plenoptic multifocal image can be applied to new eye imaging devices that specifically step the focus and/or existing devices that may or may not require the user to change the focus. The method for combining a plurality of eye images into a plenoptic multifocal image can also be applied by deliberately stepping the focus of a device to generate an image set.

In another embodiment of the present invention, the method for combining a plurality of eye images into a plenoptic multifocal image utilizes a variety of eye imaging modalities (alone or in combination) including but not limited to one or more slit lamp mounted cameras, one or more slit lamp integrated cameras, OCT, optical imaging at specific wavelengths, multispectral imaging, hyper spectral imaging, autofluorescence imaging, confocal retinal imaging, scanning laser ophthalmoscopy, adaptive optics imaging, polarization orientation specific imaging, one or more fundus cameras, one or more hand held imagers, one or more direct ophthalmoscopes and one or more indirect ophthalmoscopes, fluorescein angiography, ICG angiography, curcumin fluorescence imaging, autofluorescence and other eye imaging modalities. Image data sets are acquired either with random or deliberate focus and exposure control. Image data sets are automatically registered with sub-pixel accuracy. Image processing is performed on data sets to identify clear, well-exposed portions of data sets and eliminate relatively poorly defined and/or dark data sets or other aberrations that degrade imaging quality. Good or well-suited image data is then recombined into a single image that is plenoptic or in focus at multiple depths and/or a movie file is created that allows the user to step through a focus stack or select a region that they want to view that is in focus. The term "step through selected regions" is defined as to change the focal position of interest. The term step through selected regions is similar to scrolling through frames in a movie. Stepping through a focus stack involves changing the viewed image from a collected sequence of frames where the focus is changed between each frame. A multi-focus sequence of images can be formed by changing the focus between each collected frame. Each image is then an optical-slice of the object.

In another embodiment of the present invention, a micro-lens array can be used to collect the light-field of a scene, which allows the focus to be changed post-acquisition, and thus a multi-focus stack can be calculated. The image is collected using one or more high density camera sensors (e.g. one or more CCD or CMOS sensors) or one or more point and line scanning devices. The resulting image stack will have a lower resolution compared to the source images when using a micro-lens array. The multiple image planes contain the in-focus structures from the corresponding focal plane in the specimen. Out-of-focus information from surrounding structures will also contaminate the image collected. In one embodiment of the present invention, the method for combining a plurality of eye images into a plenoptic multifocal image generates an image data set obtained from existing eye imaging devices.

In another embodiment of the present invention, the method for combining a plurality of eye images into a plenoptic multifocal image generates a plurality of image data sets obtained from new eye imaging devices specifically designed to create images that are in focus at various depths either through stepping focus or a multi-element microlens that is placed over a sensor that contains information from multiple image planes.

In another embodiment of the present invention, the method for combining a plurality of eye images into a plenoptic multifocal image is applied to one or more OCT data sets to obtain one or more relatively clear comprehensive OCT data sets.

Figure 3:
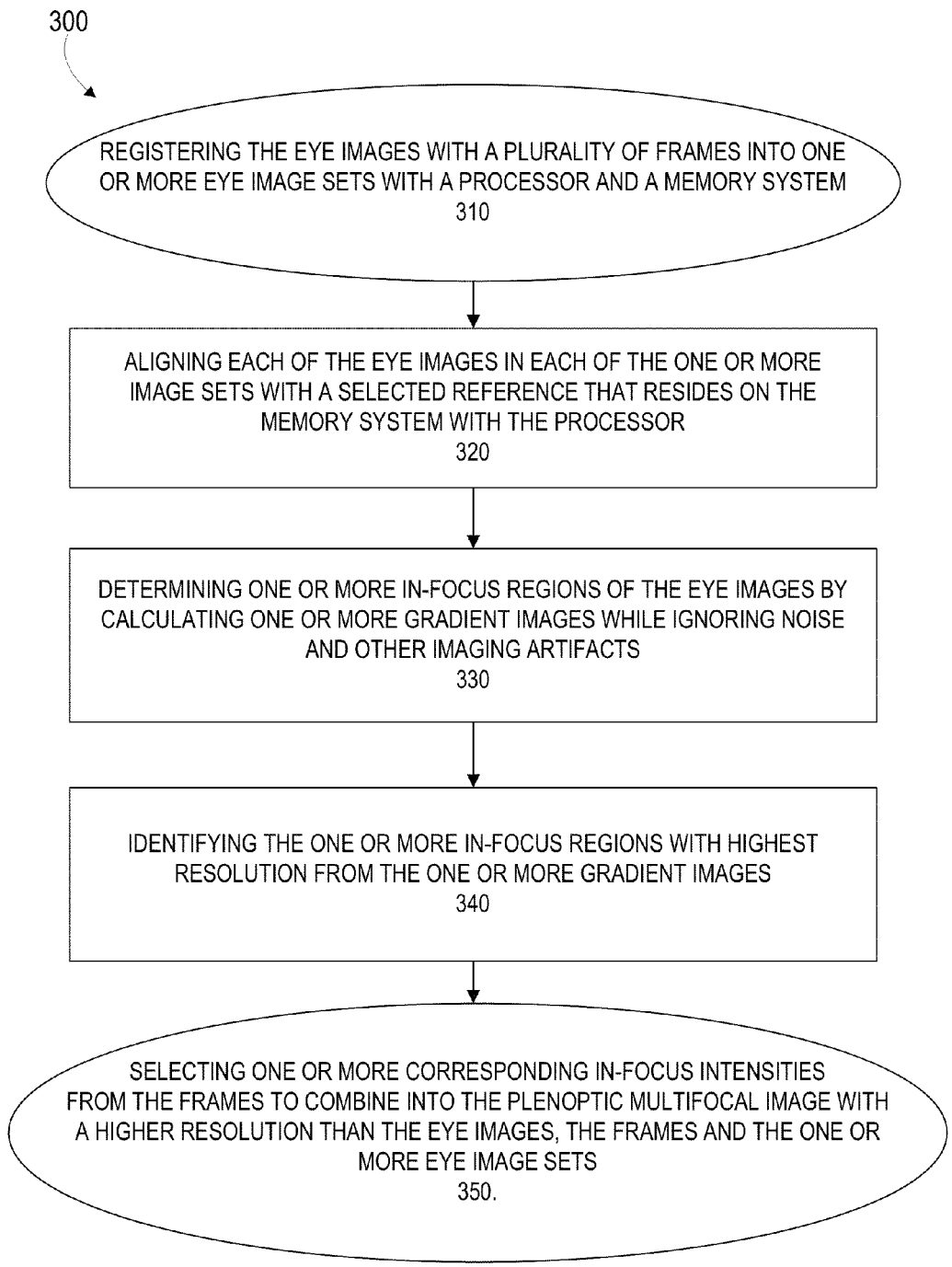
FIG. 3 illustrates a flowchart of a first method for combining a plurality of eye images into a plenoptic multifocal image, in accordance with one embodiment of the present invention.

FIG. 3 illustrates a flowchart of a first method for combining a plurality of eye images into a plenoptic multifocal image 300, in accordance with one embodiment of the present invention.

The first method 300 for combining a plurality of eye images into a plenoptic multifocal image includes the steps of registering the eye images with a plurality of frames into one or more eye image sets with a processor and a memory system 310, aligning each of the eye images in each of the one or more image sets with a selected reference that resides on the memory system with the processor 320, determining one or more in-focus regions of the eye images by calculating one or more gradient images while ignoring noise and other imaging artifacts 330, identifying the one or more in-focus regions with highest resolution from the one or more gradient images 340 and selecting one or more corresponding in-focus intensities from the frames to combine into the plenoptic multifocal image with a higher resolution than the eye images, the frames and the one or more eye image sets 350.

The registering step 310 is controlled by a predetermined quantity of control points, where the predetermined quantity of control points is manually set by user observation or is automatically calculated by the processor. The processor utilizes an image processing algorithm to automatically calculate the predetermined quantity of control points. The eye images, the frames, the image sets and the predetermined quantity of control points reside on the memory system. The aligning step 320 includes that the eye images are collected using one or more high density camera sensors. The one or more high density camera sensors are one or more charge coupled device sensors or CCD sensors or the one or more high density camera sensors are one or more complementary metal oxide semiconductor sensors or CMOS sensors, or one or more point and line scanning devices. The determining step 330 includes that the eye images are combined by taking the one or more in-focus points with highest resolution from each of the eye images. The identifying step 340 includes that the eye images are combined by taking the most in-focus point in each of the eye images. The eye images are combined by averaging multiple in-focus regions to improve a signal-to-noise ratio or SNR. The plenoptic multifocal image is generated by one or more traditional eye imaging modalities or devices selected from the group of one or more slit lamp mounted cameras, one or more slit lamp integrated cameras, optical coherence tomography, optical imaging at specific wavelengths, multispectral imaging, hyper spectral imaging, autofluorescence imaging, confocal retinal imaging, scanning laser ophthalmoscopy, one or more adaptive optics devices, one or more polarization orientation specific devices, one or more fundus cameras, one or more hand held imagers, one or more direct and indirect ophthalmoscopes, fluorescein angiography, ICG angiography and curcumin fluorescence imaging, or autofluorescence.

The selecting step 350 identifies the one or more in-focus regions that are well-focused, evenly illuminated and obtains high frequency image information to recombine the processed images into the plenoptic multifocal image. The plurality of eye images may be a larger montage image made of a plurality of individual optimized frames. The high frequency image information is calculated by removing one or more low frequency image components and by smoothing and suppressing one or more random noise variations. The method 300 is applied by stepping focus to generate the one or more eye image sets. The method 300 also creates the images that are in focus at various depths through the stepping focus.

Figure 4:
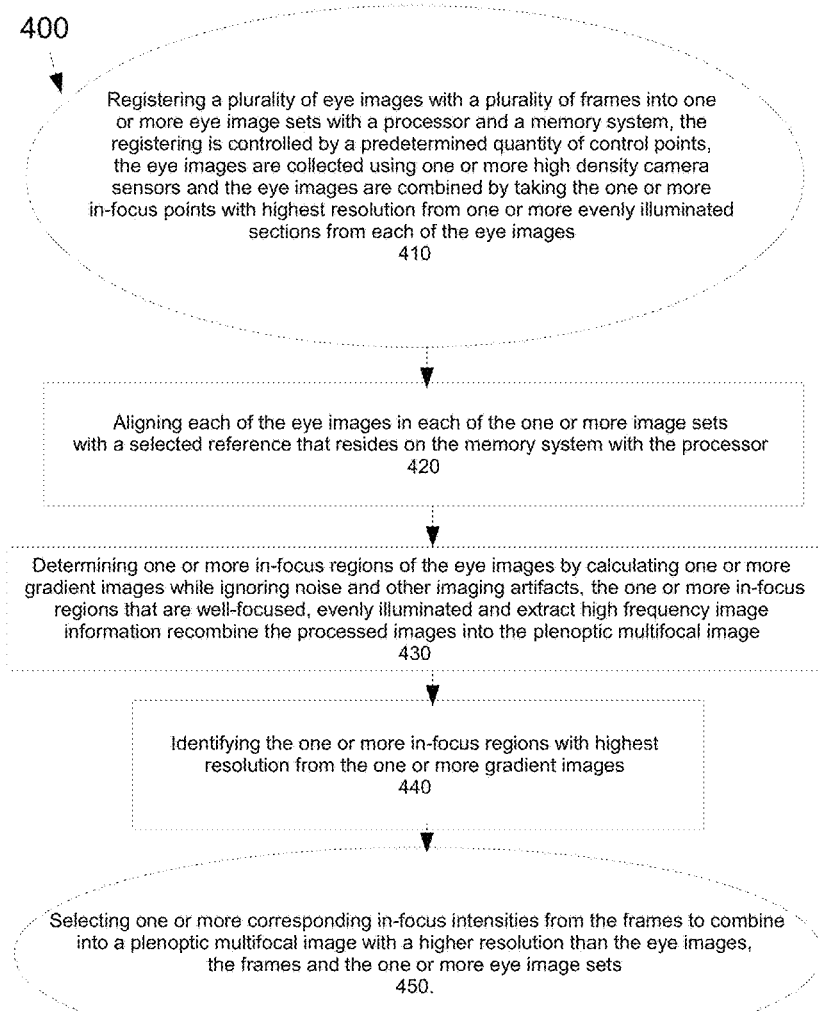
FIG. 4 illustrates a flowchart of a second method for combining a plurality of eye images into a plenoptic multifocal image, in accordance with one embodiment of the present invention.

FIG. 4 illustrates a flowchart of a second method for combining a plurality of eye images into a plenoptic multifocal image 400, in accordance with one embodiment of the present invention.

The second method 400 includes the steps of registering a plurality of eye images with a plurality of frames into one or more eye image sets with a processor and a memory system, the registering is controlled by a predetermined quantity of control points, the eye images are collected using one or more high density camera sensors and the eye images are combined by taking the one or more in-focus points with highest resolution from one or more evenly illuminated sections from each of the eye images 410, aligning each of the eye images in each of the one or more image sets with a selected reference that resides on the memory system with the processor 420, determining one or more in-focus regions of the eye images by calculating one or more gradient images while ignoring noise and other imaging artifacts, the one or more in-focus regions that are well-focused, evenly illuminated and obtain high frequency image information recombine the processed images into the plenoptic multifocal image 430, identifying the one or more in-focus regions with highest resolution from the one or more gradient images 440 and selecting one or more corresponding in-focus intensities from the frames to combine into a plenoptic multifocal image with a higher resolution than the eye images, the frames and the one or more eye image sets 450.

The second method for combining a plurality of eye images into a plenoptic multifocal image 400 illustrated and described in FIG. 4 and its description is similar to the first method for combining a plurality of eye images into a plenoptic multifocal image 300 illustrated and described in FIG. 3 and its description. In contrast, the second method for combining a plurality of eye images into a plenoptic multifocal image 400 includes the one or more high density camera sensors or one or more point and line scanning devices. Additionally, the one or more in-focus regions are well-focused, evenly illuminated and obtain high frequency image information using a frequency domain filter or a Weiner filter and recombine the processed images into the one or more images.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A method for combining a plurality of eye images into a plenoptic multifocal image, comprising:
    registering a plurality of eye images with a plurality of frames into one or more eye image sets with a processor and a memory system;
    aligning each of the eye images in each of the one or more image sets with a selected reference that resides on the memory system with the processor;
    determining one or more in-focus regions of the eye images by calculating one or more gradient images while ignoring noise and other imaging artifacts;
    identifying the one or more in-focus regions with highest resolution from the one or more gradient images; and
    selecting one or more corresponding in-focus intensities from the frames to combine into a plenoptic multifocal image with a higher resolution than the eye images, the frames and the one or more eye image sets.

2. The method according to claim 1, wherein the registering is controlled by a predetermined quantity of control points.

3. The method according to claim 2, wherein the predetermined quantity of control points are manually set by user observation.

4. The method according to claim 2, wherein the predetermined quantity of control points are automatically calculated by the processor.

5. The method according to claim 1, wherein the eye images, the frames, the predetermined quantity of control points and the image sets reside on the memory system.

6. The method according to claim 1, wherein the eye images are collected using one or more high density camera sensors.

7. The method according to claim 6, wherein the one or more high density camera sensors are one or more charge coupled device sensors.

8. The method according to claim 6, wherein the one or more high density camera sensors are one or more complementary metal oxide semiconductor sensors.

9. The method according to claim 1, wherein the eye images are combined by taking the one or more in-focus points with highest resolution from one or more evenly illuminated sections from each of the eye images.

10. The method according to claim 1, wherein the eye images are combined by averaging the multiple in-focus regions to improve a signal-to-noise ratio.

11. The method according to claim 1, wherein the plenoptic multifocal image is generated by one or more traditional eye imaging modalities or devices selected from the group of one or more slit lamp mounted cameras, one or more slit lamp integrated cameras, optical coherence tomography, optical imaging at specific wavelengths, multispectral imaging, hyper spectral imaging, autofluorescence imaging, confocal retinal imaging, scanning laser ophthalmoscopy, one or more adaptive optics devices, one or more polarization orientation specific devices, one or more fundus cameras, one or more hand held imagers, one or more direct and indirect ophthalmoscopes, fluorescein angiography, ICG angiography, curcumin fluorescence imaging, and autofluorescence.

12. The method according to claim 1, wherein the method is applied by stepping focus to generate the one or more eye image sets.

13. The method according to claim 12, wherein the method creates the images that are in focus at various depths through the stepping focus.

14. The method according to claim 1, wherein the method identifies the one or more in-focus regions that are well-focused, evenly illuminated and obtain high frequency image information to recombine the processed images into the plenoptic multifocal image.

15. The method according to claim 14, wherein the high frequency image information is calculated by removing one or more low frequency image components and by smoothing and suppressing one or more random noise variations.

16. A method for combining a plurality of eye images into a plenoptic multifocal image, comprising:
    registering a plurality of eye images with a plurality of frames into one or more eye image sets with a processor and a memory system, the registering is controlled by a predetermined quantity of control points, the eye images are collected using one or more high density camera sensors and the eye images are combined by taking the one or more in-focus points with highest resolution from one or more evenly illuminated sections from each of the eye images;
    aligning each of the eye images in each of the one or more image sets with a selected reference that resides on the memory system with the processor;
    determining one or more in-focus regions of the eye images by calculating one or more gradient images while ignoring noise and other imaging artifacts, the one or more in-focus regions that are well-focused, evenly illuminated and obtain high frequency image information recombine the processed images into the plenoptic multifocal image;
    identifying the one or more in-focus regions with highest resolution from the one or more gradient images; and selecting one or more corresponding in-focus intensities from the frames to combine into a plenoptic multifocal image with a higher resolution than the eye images, the frames and the one or more eye image sets.

17. The method according to claim 16, wherein the predetermined quantity of control points are manually set by user observation.

18. The method according to claim 16, wherein the predetermined quantity of control points are automatically calculated by the processor.

19. The method according to claim 16, wherein the eye images, the frames, the predetermined quantity of control points and the image sets reside on the memory system.

20. The method according to claim 16, wherein the one or more high density camera sensors are one or more charge coupled device sensors.

21. The method according to claim 16, wherein the one or more high density camera sensors are one or more complementary metal oxide semiconductor sensors.

22. The method according to claim 16, wherein the eye images are collected using one or more point and line scanning devices.

23. The method according to claim 16, wherein the eye images are combined by averaging the one or more in-focus regions to improve a signal-to-noise ratio.

24. The method according to claim 16, wherein the one or more in-focus regions are well-focused, evenly illuminated and obtain high frequency image information using a frequency domain filter and recombine the processed images into the one or more images.

25. The method according to claim 16, wherein the one or more in-focus regions are well-focused, evenly illuminated and obtain high frequency image information using a Weiner filter and recombine the processed images into the one or more images.

26. The method according to claim 16, wherein the plenoptic multifocal image is generated by one or more traditional eye imaging modalities or devices selected from the group of one or more slit lamp mounted cameras, one or more slit lamp integrated cameras, optical coherence tomography, optical imaging at specific wavelengths, multispectral imaging, hyper spectral imaging, autofluorescence imaging, confocal retinal imaging, scanning laser ophthalmoscopy, one or more adaptive optics devices, one or more polarization orientation specific devices, one or more fundus cameras, one or more hand held imagers, one or more direct and indirect ophthalmoscopes, fluorescein angiography, ICG angiography, curcumin fluorescence imaging, and autofluorescence.

27. The method according to claim 16, wherein the method is applied by stepping focus to generate the one or more eye image sets.

28. The method according to claim 27, wherein the method creates the images that are in focus at various depths through the stepping focus.

29. The method according to claim 16, wherein the high frequency image information is calculated by removing one or more low frequency image components and by smoothing and suppressing one or more random noise variations.

* * * * *